United States Patent [19]

Lackney

[11] Patent Number: 5,085,634
[45] Date of Patent: Feb. 4, 1992

[54] MEDICAMENT AND SUPPORT

[76] Inventor: Albert M. Lackney, 1795 TR 320 SE, Crooksville, Ohio 43731

[21] Appl. No.: 584,601

[22] Filed: Sep. 19, 1990

[51] Int. Cl.[5] .............................................. A61J 7/00
[52] U.S. Cl. ...................................................... 604/77
[58] Field of Search ............... 604/890.1, 1, 48, 77, 604/93; 424/435, 439, 440; 426/134, 75; D1/102, 105

[56] References Cited

U.S. PATENT DOCUMENTS

| D. 274,859 | 7/1984 | Harris et al. | |
| 589,712 | 9/1897 | Fouquier | 604/77 |
| 988,120 | 3/1919 | Lott | 604/93 |
| 1,298,616 | 3/1919 | Wilson | 604/77 |
| 1,593,858 | 6/1926 | Venable. | |
| 1,720,190 | 7/1929 | Van Horne. | |
| 1,847,415 | 3/1932 | Snell. | |
| 2,491,274 | 12/1949 | McNeill | 604/1 |
| 2,503,550 | 8/1957 | Ackalusky. | |
| 2,857,908 | 10/1958 | Cornfield. | |
| 2,872,925 | 2/1959 | Lindahl | 604/77 |
| 2,950,200 | 8/1960 | Jones et al. | |
| 3,426,755 | 2/1969 | Clegg | 604/77 |
| 3,875,940 | 4/1975 | Beuther | 604/77 |
| 4,365,631 | 12/1982 | Kline | 604/93 |
| 4,430,075 | 2/1984 | Urban et al. | 604/77 |
| 4,551,329 | 11/1985 | Harris et al. | |

FOREIGN PATENT DOCUMENTS 0346219 1/1905 France ............................. 604/77

OTHER PUBLICATIONS

Dyer, *Medicated Candies*, Q.S. Magazine, vol. No. 1-No. 4, Apr. 1952.

Primary Examiner—John D. Yasko
Assistant Examiner—Sharon Finkel
Attorney, Agent, or Firm—Killworth, Gottman, Hagan & Schaeff

[57] ABSTRACT

An oral medicament adapted to be administered on a support which allows sucking of the medicament while preventing inadvertent swallowing of the medicament in its entirety or in large pieces, as well as preventing accidental swallowing of the support is provided. The support includes a generally flat stick of flexible plastic material having first and second ends. The medicament is secured to the first end of the support by a frame including one cavity therein or various voids created by circular discs atop pedestals on a flat disc with raised rings. A guard may optionally be attached to the support or the support turned at a right angle for further protection against accidental swallowing of the support.

9 Claims, 2 Drawing Sheets

MEDICAMENT AND SUPPORT

BACKGROUND OF THE INVENTION

This invention relates to the combination of an oral medicament and a support therefor, and more particularly to a means for securing a medicament to a support which facilitates sucking on the medicament while preventing the medicament from breaking off from the support in its entirety or in large pieces which could cause choking, and further to a support which provides protection against accidental swallowing.

There are several types of common medicaments which are intended to be sucked or dissolved slowly in the mouth rather than swallowed whole like a pill. Such medicaments include cough drops, throat lozenges, and the like. However, such forms of medication may be unsuitable for small children or older patients, as large pieces of the medication might dissolve free and become lodged in the throat, causing choking. Additionally, the medication could accidentally be swallowed whole, causing choking or blockage of the throat cavity.

A solution to this problem is to supply the medication in the form of a lollipop or sucker in which the body of the medicament is secured to the end of a stick to facilitate sucking or chewing on the medication. If the medicament is not adequately secured to the stick, it may become separated from the stick and swallowed whole. A danger also exists in that if the user were in a reclined position while holding the stick, the stick could become lodged in the throat.

Several attempts have been made to overcome these Problems. For example, Snell, U.S. Pat. No. 1,847,415, relates to a holder for candy suckers in which a guard at the upper end is embedded in the candy. The support for the candy comprises a flexible, bendable wire so that if the user would happen to fall while sucking on the stick, the flexible support would prevent the stick from becoming lodged in the throat. However, large pieces of the candy may still be able to break off from the wire and could become lodged in the throat.

Cornfield U.S. Pat. No. 2,857,908 describes a tongue depressor which is coated with a candied confection. The depressor is shown to contain three holes in its upper portion where the candy is secured to the depressor. However, there are still large areas where the candy remains unsecured and could become free of the depressor. The holes are only effective if both sides of the medication remain and work as a unit. For example, if the lower portion were to dissolve first, the upper portion would be able to break off. Further, there is no safety feature on the stick which would prevent the stick from becoming lodged in the throat.

Harris et al, U.S. Pat. No. 4,551,329 describes an oral medicament in a lollipop shape which is supported on a handle comprising a stick of resilient material looped into a single coil with spring arms extending into enlarged ears on which the medicament is molded. The handle is designed such that if the medicament becomes separated from the ears, the released spring arms will spring apart to block entry of the handle into the throat. However, there is a possibility that large pieces of the medicament could break off from the stick and, due to the spring action, be propelled and lodged in the throat. Further, there is no safety feature on the stick which would block entry of the handle into the throat while the medicament is secured to the stick.

Accordingly, there remains a need in the art for an oral medicament which may be administered on a support without the problem of the medication breaking off in its entirety or in large pieces, and further prevents the support from becoming lodged in the throat.

SUMMARY OF THE INVENTION

The present invention meets that need by providing a means for securing an oral medicament to a support which allows sucking of the medicament while previously inadvertent swallowing of the medicament in its entirety or in large pieces, as well as preventing accidental swallowing of the support.

According to one aspect of the present invention, an elongated support is provided which includes means for securing a medicament. The support comprises an elongated generally flat stick having a first end and a second end having a rounded edge. The support also includes a frame attached to the first end of the support, the frame having at least one cavity therein and a plurality of orifices on the surface thereof communicating with the cavity. In one embodiment of the invention, a flattened spherical frame is attached to the first end of the stick, which frame has a plurality of orifices therein for securing the medicament. Preferably, the medicament in liquid form may be poured into the spherical frame through the orifices and solidified to cover the frame. Thus, the medicament forms an interlocking bond through the orifices and is held securely to the support, preventing the medicament from breaking off in its entirety, and preventing large pieces from breaking off. The medicament will be slowly dissolved in the mouth of the user.

Optionally, a notched edge is provided on the support adjacent the spherical frame for securing a safety guard. The safety guard comprises a round plate with a slit in its middle portion which may be slidably attached to the notched edge of the support to prevent accidental swallowing of the support. The opposite end of the support also optionally includes a hole therein to provide a means for grasping the support in the event of an accident.

In another embodiment of the invention, the support comprises a generally flat stick turned at an angle, preferably substantially at a right angle, at its middle portion to prevent the support from being accidentally swallowed. The support includes a first end and a second end having a rounded edge. The first end includes a generally circular frame attached thereto having a plurality of raised pedestals which create a series of voids within the frame for securing the medicament. Thus, the medicament forms an interlocking bond through the voids between the pedestals and is held securely to the support. The second end of the support also optionally includes a hole therein to provide a means for grasping the support in the event of an accident.

In a further embodiment of the invention, the support comprises a generally flat stick having a first end and a second end having a rounded edge, the first end including a generally flat disc including at least one raised area attached thereto. The medicament, in a disc-shaped form, may be secured to the front and/or back sides of the disc through indentations on the surface of the medicament which mate with the raised area on the disc. In a preferred form of the invention, the raised area is a rib or ring. The medicament may be secured to the disc by bonding or gluing using a food grade adhesive. The support may also include a notched edge for securing a safety guard as well as a hole on its lower Portion.

Accordingly, it is an object of the present invention to provide means for securing an oral medicament to a support which allows sucking of the medicament while Preventing accidental swallowing of the medicament in its entirety or in large pieces, as well as preventing accidental swallowing of the support. Other objects and advantages of the invention will be apparent from the following description, the accompanying drawings and the appended claims.

DETAILED DESCRIPTION OF THE PREFERRED EMBODIMENTS

Figure 1:
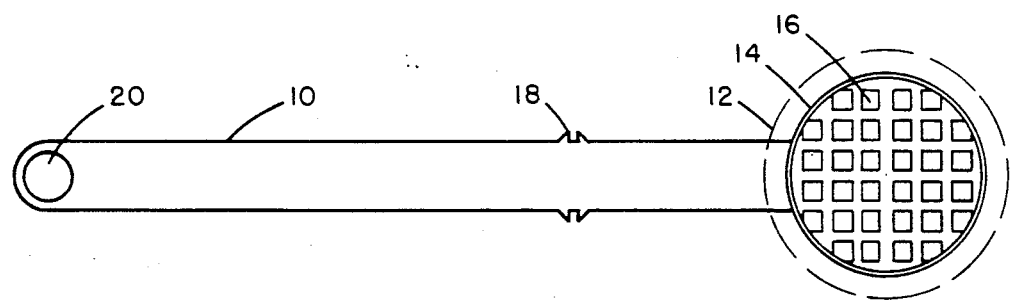
FIG. 1 is a top plan view of a medicament on a support in accordance with one embodiment of the present invention.

Reference is made to FIG. 1 of the drawings which illustrates the oral medicament secured to a support. In accordance with the present invention, an elongated support 10 is provided which includes means for securing a solid medicament 12 thereto. The support comprises a generally flat stick having a first end and a second end having a rounded edge. The support preferably comprises a flexible plastic material and can be molded as a unitary structure using techniques known in the art.

Figures 3, 4:
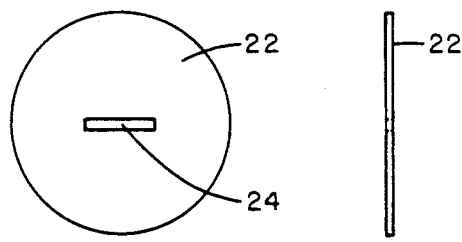
FIG. 3 is a plan view of the safety guard of the present invention.
FIG. 4 is a side view of the safety guard.

The support 10 also optionally includes notched edge 18 for securing the removable safety guard shown in FIG. 3. The second end of the support also includes a hole 20 for the purpose of providing a means for grasping or hooking onto the support in the event of an accidental swallowing.

Figure 2:
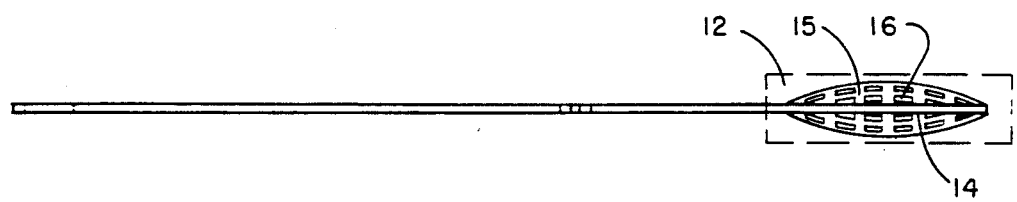
FIG. 2 is a side view of the medicament on the support of FIG. 1.

In the embodiment shown in FIGS. 1 and 2, the medicament 12 is attached to the support 10 by a flattened spherical frame 14 which is attached to the support. Preferably, the frame and support both comprise a flexible plastic material which can be molded as a unitary structure. The flattened spherical frame comprises a cavity 15 and a plurality of crosshatched holes 16 on the surface thereof. The medicament may be poured in a liquid state through the holes of the frame and solidified in a mold or by other means so as to completely fill the cavity and cover the frame. This is illustrated in the side view of the support shown in FIG. 2. The spherical frame and holes act to form multiple interlocking bonds with the medicament, thus preventing separation of the medicament from the support as well as preventing breakage (through the dissolving process) of any large pieces away from the support. For example, if the lower portion of the medicament were to dissolve first, the upper portion would remain secured due to a core of the medicament (formed within spherical frame 14) remaining within cavity 15.

Figure 5:
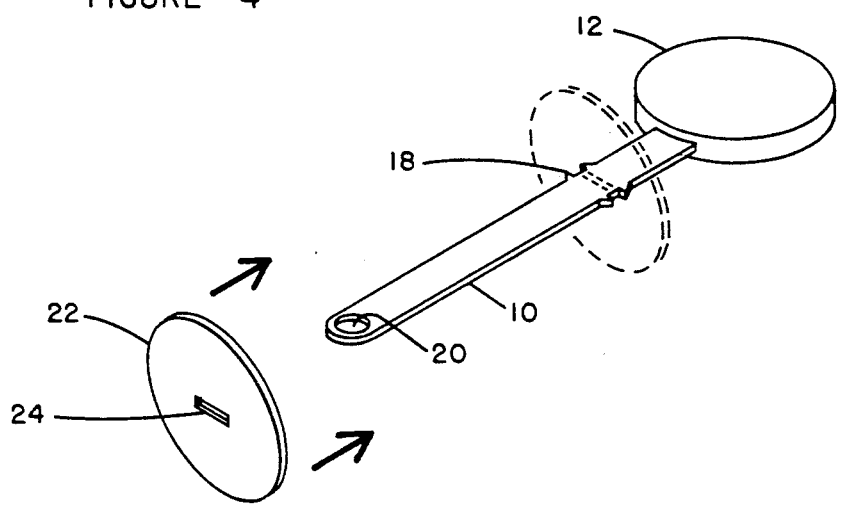
FIG. 5 is a perspective view of the medicament on the support illustrating the use of the safety guard.

FIGS. 3 and 4 illustrate the optional safety guard 22 which may be slidably attached to support 10 in order to provide a protective means which prevents the support from being forced into the user's throat. The safety guard comprises a generally round plate 22 with a slit 24 in its middle portion. As illustrated in FIG. 5, the safety guard may be mounted on the support 10 by slidably attaching it to notched edge 18 of the support where it becomes locked into place. Guard 22 may also be fabricated of a flexible plastic material.

Figure 6:
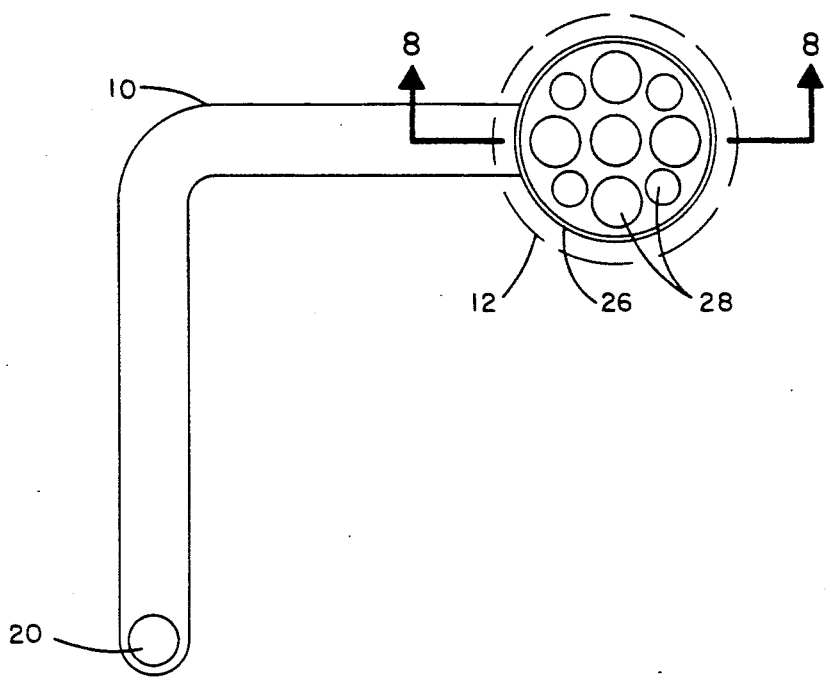
FIG. 6 is a top plan view of another embodiment of the invention.

Another embodiment of the invention is illustrated in FIG. 6 in which the support comprises a generally flat stick having a first end and a second end having a rounded edge. The support 10 is turned at an angle, preferably a right angle as illustrated, at its middle portion to prevent the support from being accidentally swallowed or forced down the throat of a user. A generally circular frame 26 is attached to the support on its first end and includes a plurality of raised pedestals 28 attached to the frame into which the liquid medicament may be poured and solidified. The support also includes a hole 20 on its lower portion to provide a means for grasping the support in the event of accidental swallowing.

Figure 7:
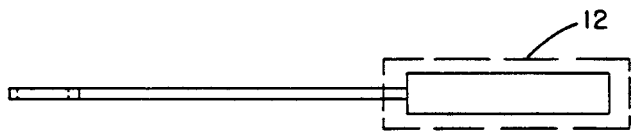
FIG. 7 illustrates a side view of the solid medicament secured to the circular frame of FIG. 6.
Figure 8:
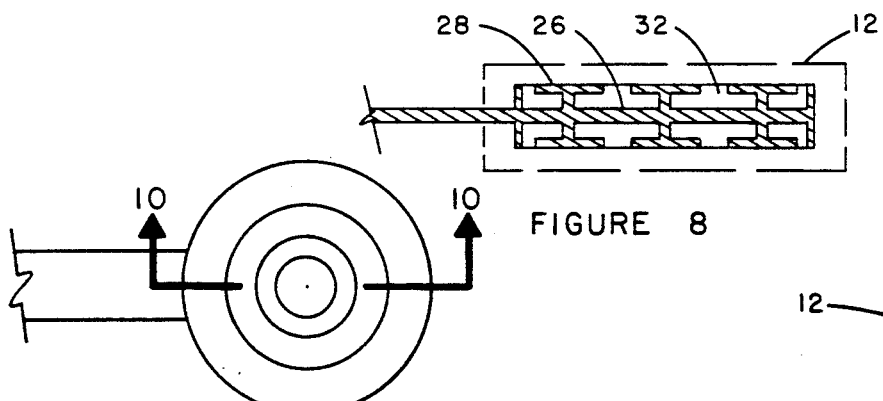
FIG. 8 is a sectional view of the circular frame taken along line 8—8 in FIG. 6.

FIG. 8 illustrates a sectional side view of the circular frame 26. As can be seen, the raised circular pedestals 28 create a cavity 32 into which the medicament may be poured. As shown in FIG. 7, the frame becomes completely coated with the solid medicament, thus forming multiple interlocking bonds which prevent separation of the medicament from the support as well as preventing breakage of any large pieces away from the support.

Figure 9:
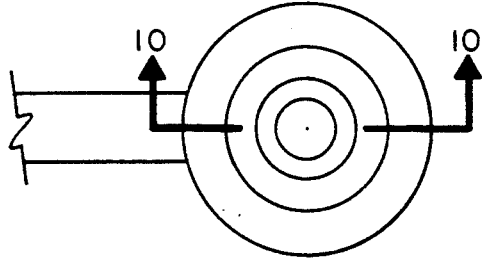
FIG. 9 is a top plan view of another embodiment of the invention.
Figure 10:
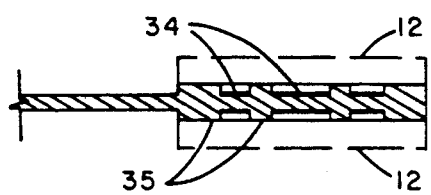
FIG. 10 is a partial side view taken along line 10—10 in FIG. 9.
Figure 11:
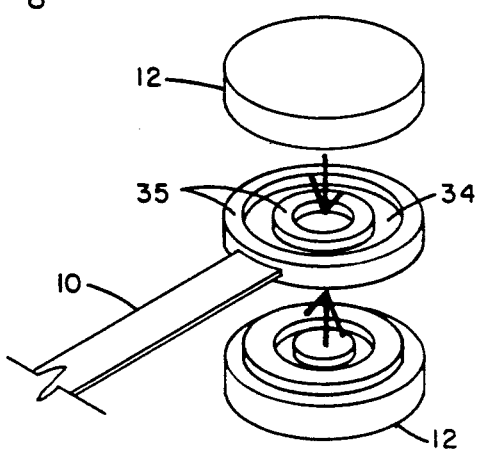
FIG. 11 is a partial perspective of the embodiment of FIGS. 9 and 10 and illustrates placement and mating of the medicament with raised areas on the disc.

FIGS. 9 through 11 illustrate yet another embodiment of the invention in which the support comprises a generally flat stick 10 as described above. Attached to the stick is a generally flat disc 34 with raised areas 35 which serve as a means for securing the medicament to the disc. As shown, these raised areas 35 may take the form of raised rings or ribs. The medicament may take the form of discs or lozenges 12, each preferably having the same diameter as the flat disc 34 and with matching indentations as the raised areas 35. The medicament discs may be secured to disc 34 with the use of a food-grade glue or other adhesive applied only the portion of medicament disc 12 making contact with disc 34. This prevents the user from dissolving the medicament to within the area of the applied glue.

It will be apparent to those skilled in the art that several different combinations of the above embodiments are possible which produce the desired safety features previously described.

Having described the invention in detail and by reference to preferred embodiments thereof, it will be apparent that modifications and variations are possible without departing from the scope of the invention defined in the appended claims.

What is claimed is:

1. In combination, an oral medicament secured to a support comprising:

a) an elongated support having first and second ends including means for securing a solid medicament thereto, said securing means comprising:
  a frame attached to said first end of said support, said frame including at least one cavity therein and a plurality of orifices on the surface thereof communicating with said cavity for securing said medicament to said support; and
b) a solid medicament filling said cavity, extending through said orifices, and substantially covering the exterior of said frame;
whereby said oral medicament secured to said support allows sucking of said medicament while presenting inadvertent swallowing of said medicament or said support.

2. The combination of claim 1 wherein said frame has a flattened spherical shape.

3. The combination of claim 1 wherein said frame is generally circular with a plurality of raised pedestals on the surface thereof, the spaces between said pedestals forming said at least one cavity.

4. The combination of claim 1 wherein said support has a notched edge adjacent said frame and means for grasping said support on said second end.

5. The oral medicament of claim 1 wherein said support includes a safety guard comprising a rounded plate with a slit in its middle portion for sliding attaching to said upper portion of said support.

6. The combination of claim 1 wherein said support comprises a flexible plastic material.

7. The combination of claim 3 wherein said pedestals comprise a generally vertical portion having a generally horizontal portion attached thereto.

8. The combination of claim 1 wherein said support is angled to prevent said support from being accidentally swallowed.

9. The combination of claim 8 wherein said angle is substantially a right angle.

* * * * *